United States Patent [19]

Ashe et al.

[11] Patent Number: 4,874,755

[45] Date of Patent: Oct. 17, 1989

[54] ANTI-INFLAMMATORY AND ANTIDEGENRATIVE COMPOUNDS ISOLATED FROM L-681,512

[75] Inventors: Bonnie M. Ashe, Scotch Plains; Daniel S. Fletcher, Bridgewater, both of N.J.

[73] Assignee: Merck & Co., Inc., Rahway, N.J.

[21] Appl. No.: 135,898

[22] Filed: Dec. 21, 1987

[51] Int. Cl.$^4$ ............................................. A61K 31/56
[52] U.S. Cl. ................... 514/179; 514/825; 514/863; 514/886
[58] Field of Search ................. 549/512; 260/397.4, 260/397.5, 397.45; 514/178, 179, 182, 825, 851, 886, 397.1, 863

[56] References Cited

U.S. PATENT DOCUMENTS 3,271,390  9/1966  Fried ................... 260/397.5
3,625,194  5/1969  Pinhas ................... 514/182

FOREIGN PATENT DOCUMENTS 0031010  3/1980  Japan ................... 514/182
0031011  3/1980  Japan ................... 514/182

OTHER PUBLICATIONS

"Isolation and Structural Elucidation of a Novel Sterol Metabolite of Fusarium Sporotrichioides", Yagen et al., J. C. S. Perkins, I, (1980), pp. 2914–2917.

Primary Examiner—Helen M. S. Sneed
Assistant Examiner—J. Saba
Attorney, Agent, or Firm—Salvatore C. Mitri; Joseph F. DiPrima

[57] ABSTRACT

There are disclosed anti-inflammatory and antidegenerative compounds which are natural products produced by cultivation of soil microorganism L-681,512 under controlled fermentation conditions.

2 Claims, 5 Drawing Sheets

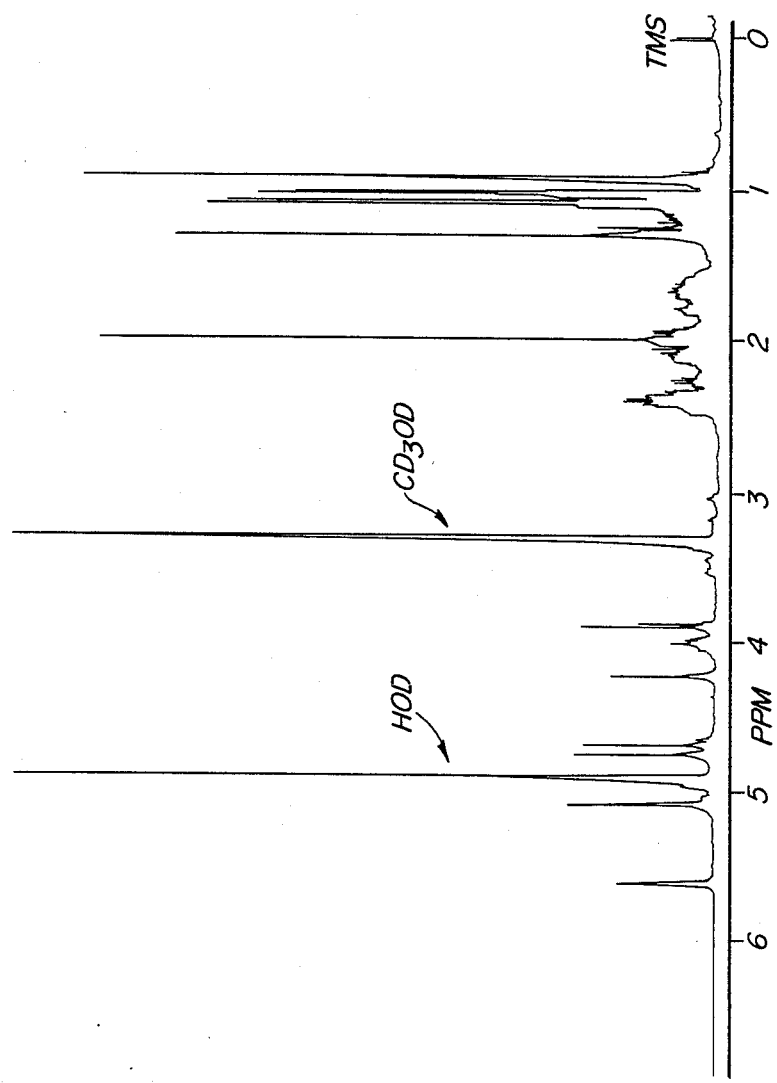
FIG-1 COMPOUND 1

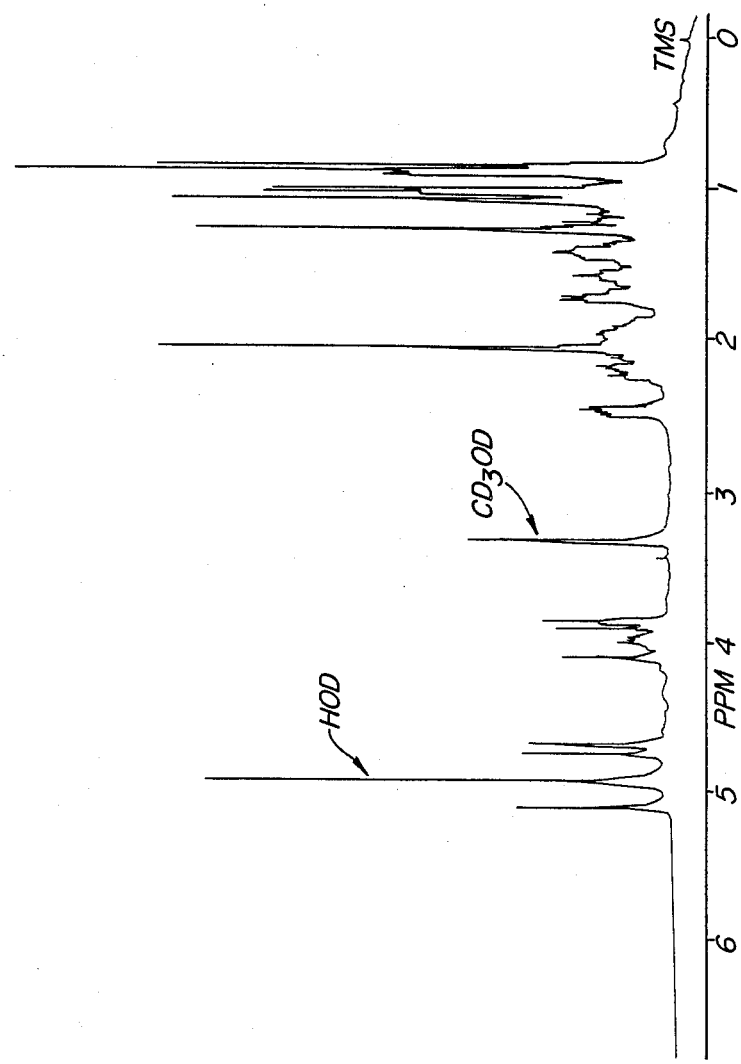
FIG-2 COMPOUND 2

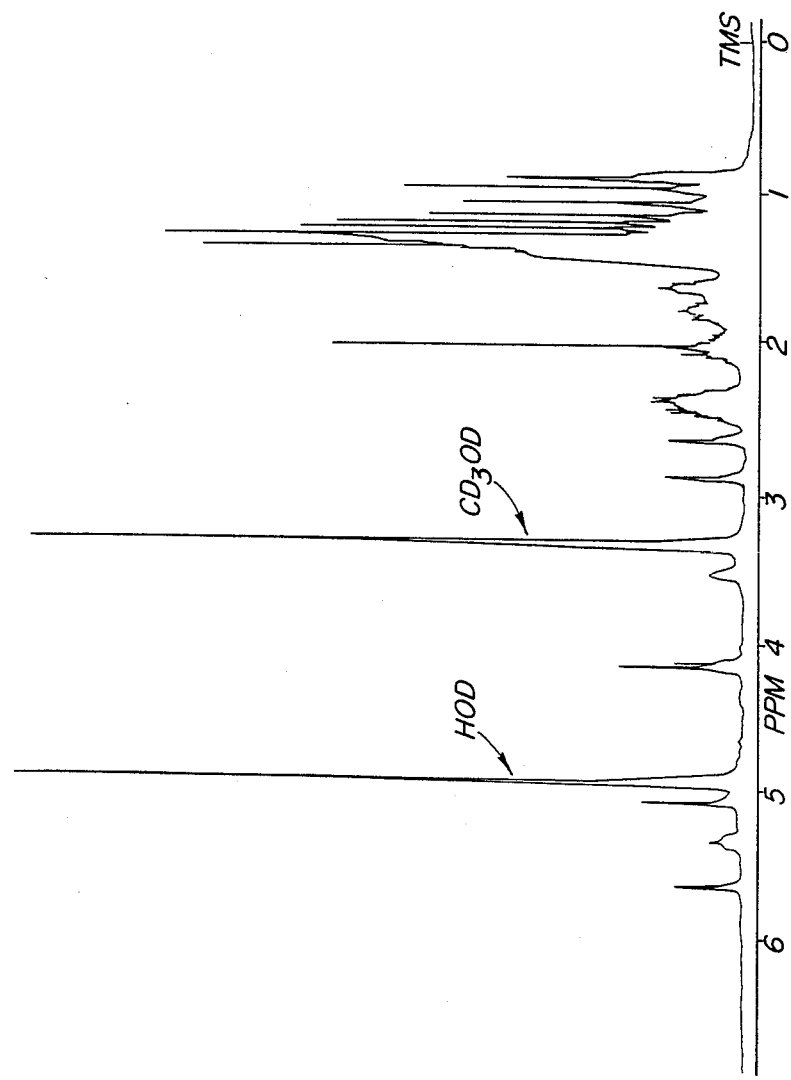

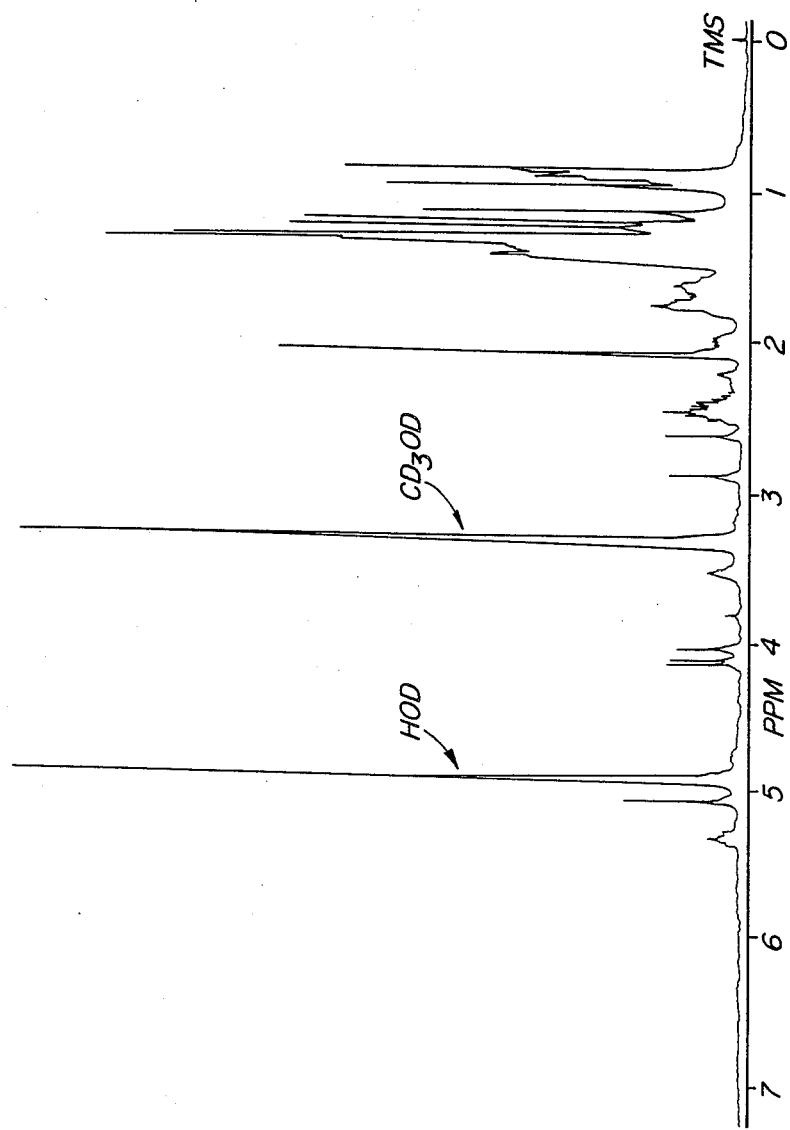

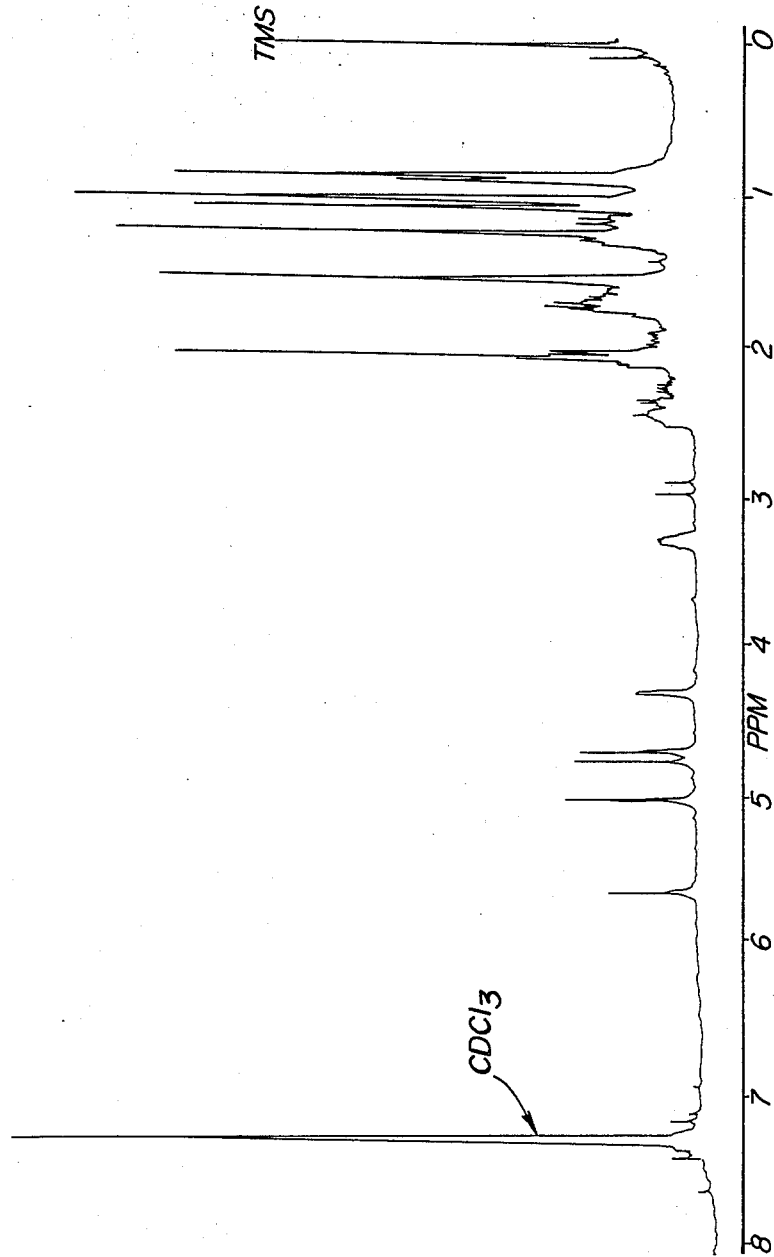
FIG-5 COMPOUND 6

ANTI-INFLAMMATORY AND ANTIDEGENRATIVE COMPOUNDS ISOLATED FROM L-681,512

BACKGROUND OF THE INVENTION

It has been found that natural compounds isolated from L-681,512 are potent elastase inhibitors and are therefore useful as anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occur during the progression of an inflammatory condition:

(1) There is a rapid production of prostaglandins (PG) and related compounds synthesized from arachidonic acid. This PG synthesis has been shown to be inhibited by aspirin related, nonsteroidal anti-inflammatory agents including indomethacin and phenylbutazone. There is some evidence that protease inhibitors prevent PG production.

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors such as, for example, N-acyl benzisothiazolones and the respective 1,1-dioxides. [Morris Zimmerman et al., *J. Biol. Chem.*, 255, 9848 (1980)].

(3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as degradation of structural proteins at the articular cartilage/pannus junction in rheumatoid arthritis, etc.

Elastase, one of these proteases, is an enzyme capable of hydrolyzing the connective tissue component elastin, a property not exhibited by the bulk of the proteases present in mammals. It acts on a protein's nonterminal bonds that are adjacent to an aliphatic amino acid Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors that block the active site of the enzyme by binding tightly thereto. Naturally occurring protease inhibitors form part of the control or defense mechanisms that are crucial to the well being of an organism. Without these control mechanisms, the proteases would destroy any protein within reach. Naturally occurring enzyme inhibitors have been shown to have appropriate configurations that allow them to bind tightly to the enzyme. This configuration is part of the reason that inhibitors bind to the enzyme so tightly [see Stroud, "A Family of Protein-Cutting Proteins", Sci. Am., July 1974, pp. 74–88]. For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema, a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. [J. C. Powers, *TIBS*, 211 (1976)].

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and, (2) a recent investigation of mechanical behavior of cartilage in response to attack by purified elastase demonstrated the direct participation of granulocyte enzymes, especially elastase, in rheumatoid cartilage destruction. [H. Menninger, et al., *Biological Functions of Proteinases*, H. Holzer and H. Tschesche, eds. Springer-Verlag, Berlin, Heidelburg, New York, pp. 196–206, 1979].

DESCRIPTION OF THE INVENTION

This invention is directed to the anti-inflammatory and antidegenerative natural compounds isolated from L-681,512 and their production by cultivation from a soil microorganism, ATCC 20858, under controlled fermentation conditions.

This invention is also directed to the sulfated and non sulfated natural product derivatives obtained from soil microorganism L-681,512, ATCC 20858, and to the methods for chemically modifying these compounds to obtain the sulfated and non-sulfated natural derivatives.

MORPHOLOGICAL AND CULTURAL CHARACTERISTICS OF ATCC 20858

A biologically pure sample of the organism from which natural compounds isolated from L-681,512 were produced has been deposited without restriction in, and made a part of, the American Type Culture Collection, Rockville, Md., from which it is available under the Accession Number ATCC 20858.

CULTURAL CHARACTERISTICS OF ATCC 20858

On Czapek-Dox agar mycelia is extensive, white and cottony becoming felted and white with sectors of faint bluish-green tinge or a pale peach tinge as the culture ages. Moist areas, faint bluish green, in color develop where microconidia are abundant.

On potato-dextrose agar mycelia is extensive, white and cottony, becoming felted and pinkish-tan in color as culture ages. When vegatative inoculum is used, moist areas, tan in color, develop where micronidia are abundant.

On Saboraud maltose agar, mycelia is extensive, velvety and deep-pinkish tan in color. Vegetative growth and medium become purpish-red.

MORPHOLOGICAL CHARACTERISTICS OF ATCC 20858

Microconidia are generally unicellar, oval-ellipsoidal, borne singly and held in a gelatinous mass. 1.9–2.4 microns × 3.6–4.8 microns.

Macronidia are 3 to 5 celled, thin-walled, ends are tapered and slightly curved. 3.6–4.8 microns × 24–36 microns.

Chlamyolospores are abundant, terminal and intercalary, globose, generally smooth walled, usually formed singly but sometimes found in pairs.

In the present invention, the antiinflammatory and antidegenerative natural compounds isolated from L-681,512 are produced by cultivation of the soil microorganism at a temperature range of from about 24° to 30° C., preferably 28° C., under controlled fermentation conditions. The composition of the nutrient medium may be varied over a wide range. The essential nutrient ingredients are: a carbon source, a nitrogen source, a phosphorus source, a sulfur source and a source of ions including: $Cl^-$, $Na^+$, $K^+$, $Ca^{2+}$ and $CO_3^{2-}$.

Cultivation is most productive under nearly neutral pH conditions, preferably within the range of 6.0–8.0.

Typical sources of carbon include, glucose, lactose, maltose, sucrose, fructose, dextrin, starches, molasses, lycerol, and the like. Typical nitrogen sources include vegetable meals (e.g., soy, peanut, corn, etc.), rice, bran, meal flours, animal viscera, various hydrolysates (casein, yeast, soybean, etc.), urea and amino acids.

The maximum yield of anti-inflammatory and antidegenerative compounds isolated from L-681,512 can be achieved within about 1 to 2 weeks of fermentation under optimum conditions. The inoculum for the fermentation may be provided from vegetative growth in a medium which supports rapid growth of the organism, such as described in Example 1 hereafter.

Following cultivation of the microorganism, elastase active compounds can be isolated from it and the isolated compounds can be chemically modified to obtain sulfated and non-sulfated natural derivatives of compound 681,512.

UTILITY OF THE COMPOUNDS WITHIN THE SCOPE OF THE INVENTION

This invention also relates to a method of treating patients (or mammals raised in the dairy, meat, or fur industries or as pets) suffering from inflammation or pain. More specifically, it relates to a method of treatment involving the administration of a compound of the invention as the active constituent.

For the treatment of inflammation and pain a compound of the invention can be administered orally, topically, parenterally, by inhalation spray or rectally in dosage unit formulations containing conventional non toxic pharmaceutically acceptable carriers, adjuvants and vehicles. The term "parenteral" as used herein includes subcutaneous injections, intravenous, intramuscular, intrasternal injection or infusion technigues. In addition to the treatment of warm-blooded animals such as horses, cattle, sheep, dogs, cats, etc., the compounds of the invention are effective in the treatment of humans.

The pharmaceutical compositions containing the active ingredient can be in a form suitable for oral use, for example, as tablets, troches, lozenges, aqueous or oily suspensions, dispersible powders or granules, emulsions, hard or soft capsules, or syrups or elixirs.

Compositions intended for oral use can be prepared according to any method known to the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Tablets containing the active ingredient in admixture with non-toxic pharmaceutically acceptable excipients can also be manufactured by known methods. The excipients used can be, for example, (1) inert diluents such as calcium carbonate, sodium carbonate, lactose, calcium phosphate or sodium phosphate; (2) granulating and disintegrating agents such as corn starch or alginic acid; (3) binding agents such as starch, gelatin or acacia, and, (4) lubricating agents such as magnesium stearate, stearic acid or talc. The tablets can be uncoated or they can be coated by known technigues to delay disintegration and absorption in the gastrointestinal tract and thereby provide a sustained action over a longer period. For example, a time delay material such as glyceryl monostearate or lyceryl distearate can be employed. The tablets can also be coated by the technigues described in U.S. Pat. Nos. 4,256,108; 4,160,452; and 4,265,874 to form osmotic therapeutic tablets for controlled release.

In some cases, formulations for oral use can be in the form of hard gelatin capsules wherein the active ingredient is mixed with an inert solid diluent such as, for example, calcium carbonate, calcium phosphate or kaolin. They can also be in the form of soft gelatin capsules wherein the active ingredient is mixed with water or an oil medium such as, for example, peanut oil, liquid paraffin, or olive oil.

Aqueous suspensions normally contain the active materials in admixture with excipients suitable for the manufacture of aqueous suspensions. Such excipients can be:

(1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents such as:
 (a) a naturally occurring phosphatide such as lecithin,
 (b) a condensation product of an alkylene oxide with a fatty acid such as polyoxyethylene stearate, (c) a condensation product of ethylene oxide with a long chain aliphatic alcohol such as heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride such as polyoxyethylene sorbitan monooleate.

The aqueous suspensions can also contain one or more preservatives such as ethyl or n-propyl p-hydroxybenzoate; one or more coloring agents; one or more flavoring agents; and, one or more sweetening agents such as sucrose or saccharin.

Oily suspension can be formulated by suspending the active ingredient in a vegetable oil, such as arachis oil, olive oil, sesame oil or coconut oil, or in a mineral oil such as liquid paraffin. The oily suspensions can contain a thickening agent such as beeswax, hard paraffin or cetyl alcohol. Sweetening agents and flavoring agents can be added to provide a palatable oral preparation. These compositions can be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those mentioned above. Additional excipients such as the sweetening, flavoring and coloring agents described above can also be present.

The pharmaceutical compositions of the invention can also be in the form of oil-in-water emulsions. The oily phase can be a vegetable oil such as olive oil or arachis oils, or a mineral oil such as liquid paraffin or a mixture thereof. Suitable emulsifying agents can be naturally-occurring gums such as gum acacia and gum tragacanth; naturally-occurring phosphatides such as soy bean and lecithin; esters or partial esters derived from fatty acids and hexitol anhydrides such as sorbitan monooleate; and, condensation products of said partial esters with ethylene oxide such as polyoxyethylene sorbitan monooleate. The emulsions can also contain sweetening and flavoring agents.

Syrups and elixirs can be formulated with sweetening agents, for example, glycerol, propylene glycol, sorbitol or sucrose. Such formulations can also contain a demulcent, a preservative and flavoring and coloring agents.

The pharmaceutical compositions can be in the form of a sterile injectable aqueous or oleagenous suspension. This suspension can be formulated according to known methods using those suitable dispersing, wetting, and suspending agents which have been mentioned above. The sterile injectable preparation can also be a sterile injectable solution or suspension in a non toxic parenterally acceptable diluent or solvent, for example, as a solution in 1,3-butane diol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are useful in the preparation of injectables.

A compound of the invention can also be administered in the form of suppositories for rectal administration of the drug. These compositions can be prepared by mixing the drug with a suitable non irritating excipient which is solid at ordinary temperatures but liquid at the rectal temperature and will therefore melt in the rectum to release the drug. Such excipients are cocoa butter and polyethylene glycols.

For topical use, creams, ointments, jellies, solutions or suspensions, etc., containing the invention compounds can be employed.

Dosage levels of the order from about 1 mg to about 100 mg per kilogram of body weight per day are useful in the treatment of the above-indicated conditions (from about 50 mg to about 5 gms. per patient per day). For example, inflammation is effectively treated and antipyretic and analgesic activity manifested by the administration from about 2.5 to about 75 mg of a compound of the invention per kilogram of body weight per day (about 75 mg to about 3.75 gms per patient per day).

The amount of active ingredient that can be combined with the carrier materials to produce a single dosage form will vary depending upon the host treated and the particular mode of administration. For example, a formulation intended for oral administration of humans can contain from 5 mg to 5 gm of active agent compounded with an appropriate and convenient amount of carrier material which can vary from about 5 to about 95 percent of the total composition. Dosage unit forms will generally contain between from about 25 mg to about 500 mg of active ingredient.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

DETAILED DESCRIPTION OF THE INVENTION

The following Examples are set forth to illustrate the cultivation of the microorganism and the isolation and chemical modification of sulfated and non-sulfated compounds derived from it.

In the Examples which follow, compounds 1–4, 6–9, 15 and 16 were obtained by isolation, compounds 10–14 were obtained by synthesis, and compound 5 was obtained by both isolation and synthesis.

All of the compounds of the invention are represented by the following general formula:

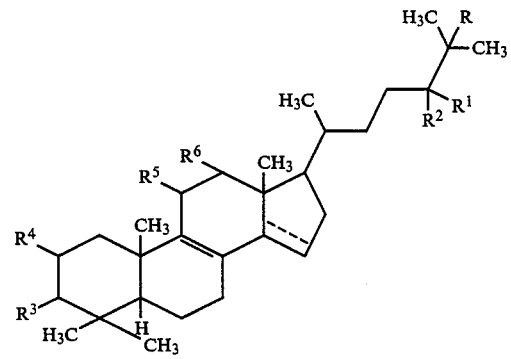

wherein:
R is OH or H;
$R^1$ and $R^2$ together form $=CH_2$, $—CH_2O—$;

$R^3$ is H, OH, $HSO_3O$, $HOCOCH_2CH_2CO_2$;
$R^4$ is OH, $HOC_{15}H_{30}CO_2$, AcO, or is H;
$R^5$ is O=, OH, AcO; and
$R^6$ is

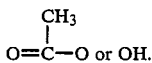

O=C—O or OH.

EXAMPLE 1

Isolation and Cultivation of the Culture Producing L-681,512

1. Soil Isolation

| Isolation Medium | |
| --- | --- |
| Baltimore Biological Laboratory | |
| (BBL) Czapek Dox agar | 50 g |
| Yeast extract from Difco | 5 g |
| agar | 5 g |
| distilled water | 1000 ml |
| 50 μg/ml of cefoxitin was added when cooled. | |

The soil sample (5 mg) was added to test tubes containing 10 ml of soil isolation medium. After mixing, the contents of each test tube was poured into a 100 mm petri plate. The plates were incubated at 28° C. for two weeks and were examined every day for the growth of fungi. The cultivated fungi were isolated by means of an agar plug maker and were transferred to potato dextrose agar plates. These plates were incubated at 28° C. for seven days and the cultivated fungi were then transferred to potato dextrose agar slants. These slants were incubated at 28° C. for seven days and were stored in the cold until needed.

2. First Fermentation

| Fermentation Medium | |
| --- | --- |
| corn steep liquor | 5 g |
| tomato paste | 40 g |
| oatmeal | 10 g |
| cerelose | 10 g |
| *trace element mix #2 | 10 ml |
| distilled water | 1000 ml |
| Adjust pH to 6.8. with NaOH | |

Seed Stage: A 250 ml flask of fermentation medium (containing 50 ml of medium) was inoculated with spores from a slant and was incubated for three days at 28° C. on a rotary shaker at 220 rpm.

1. Production Stage: Two ml of the seed was transferred to a fresh 250 ml flask of fermentation medium which was incubated at 28° C. and 220 rpm for five days. The entire sample was submitted for assay of elastase inhibition.

2. First Regrowth: The seed stage was grown in the same manner as described above. Two ml of seed was transferred to each of four 250 ml flasks of fresh fermentation medium which were then incubated at 28° C. and 220 rpm for three, five, seven and ten days. One flask was harvested and delivered for activity assay.

| *TRACE ELEMENT MIXTURE #2 | |
| --- | --- |
| $FeSO_4.7H_2O$ | 10 mg |
| $MnSO_4.4H_2O$ | 10 mg |
| $CuCl_2.2H_2O$ | 0.25 mg |

| *TRACE ELEMENT MIXTURE #2 (continued) | |
| --- | --- |
| $CaCl_2$ | 1.0 mg |
| $H_3BO_3$ | 0.56 mg |
| $(NH_4)_6MoO_4$—$4H_2O$ | 0.19 mg |
| $ZnSO_4.7H_2O$ | 2 mg |
| Distilled Water | 1 liter |

3. Second Regrowth

Seed Stage: The fungus producing the containing compounds was transferred from a fresh YME slant (yeast extract, malt extract peptrase agar medium) to two 250 ml flasks of fermentation medium which were then incubated at 28° C. and 220 rpm for three days.

Production Stage: Two liters of the culture were grown in a combination of 250 ml and 500 ml flasks.

Two (2) ml of seed was transferred to each of twenty 250 ml flasks (containing 50 ml of fermentation medium). They were incubated for five days at 28° C. and 220 rpm and were then pooled into one flask.

Ten (10) ml of seed was transferred to each of four 500 ml flasks (containing 250 ml of fermetation medium). They were incubated for five days at 28° C. and 220 rpm and were then pooled into one flask.

Two (2) ml aliquots of both of the above samples were delivered for assay of elastase inhibition and and 800 ml were delivered for chemical isolation.

EXAMPLE 1-A

14-Liter Production of L-681, 512-004 in Stirred Fermentation Vessels

| Fermentation Medium KF | |
| --- | --- |
| Tomato paste | 40 g |
| Oat flour | 10 g |
| Corn steep liquor | 5 g |
| Dextrose | 10 g |
| *Trace element mixture | 10 ml |
| Distilled water | |
| Adjusted to pH 6. | |

Seed stage - 1: A 1 cm×1 cm section of a well sporulated slant, CAJ20, was inoculated into a 250 ml unbaffled erlenmeyer flask containing 50 ml of KF medium sterilized for 20 minutes at 121° C. This flask was cultivated for 72 hours at 28° C. with shaking on a rotary shaker at 220 rpm.

Seed stage - 2: 15 ml of the above inoculum were used to innoculate a second stage seed flask (2-liter unbaffled erlenmeyer flask containing 500 ml of KF medium). The second stage seed was cultivated for 48 hours at 28° C. with shaking on a rotary shaker at 220 rpm.

Production tank: The entire contents of seed stage 2 flask was used to inoculate a 14-liter New Brunswick Scientific fermentor containing 9.5 liters of KF medium. The culture was then cultivated for 144 hrs at 28° C. at an air flow of 3.0 L/minute, and an agitation of 400 rpm.

| *Trace element mixture | |
| --- | --- |
| $FeSO_4.7H_2O$ | 1 g |
| $MnSO_4.4H_2O$ | 1 g |
| $CoCl_2.2H_2O$ | 0.025 g |
| $CaCl_2$ | 0.1 g |
| $H_3BO_3$ | 0.056 g |
| $(NH_4)_6Mo_7O_2.4H_2O$ | 0.019 g |

-continued

| *Trace element mixture | |
|---|---|
| $ZnSO_4.7H_2O$ | 0.2 g |
| distilled water | 1000 ml |

EXAMPLE 1-B

14-Liter Production of L-681, 512–007 in Stirred Fermentation Vessels

| Fermentation Medium KF | |
|---|---|
| Tomato paste | 40 g |
| Oat flour | 10 g |
| Corn steep liquor | 5 g |
| Dextrose | 10 g |
| *Trace element mixture | 10 ml |
| Distilled water | |
| Adjusted to pH 6. | |

Seed stage - 1: A 1 cm × 1 cm section of a well sporulated slant, CAJ20, was inoculated into a 250 ml unbaffled erlenmeyer flask containing 50 ml of KF medium sterilized for 20 minutes at 121° C. This flask was cultivated for 72 hours at 28° C. with shaking on a rotary shaker at 220 rpm.

Seed stage - 2: 15 ml of the above inoculum were used to innoculate a second stage seed flask (2-liter unbaffled erlenmeyer flask containing 500 ml of KF medium). The second stage seed was cultivated for 48 hours at 28° C. with shaking on a rotary shaker at 220 rpm.

Production tank: The entire contents of seed stage 2 flask was used to inoculate a 14 liter New Brunswick Scientific fermentor containing 9.5 liters of KF medium. The culture was then cultivated for 114 hrs at 28° C. at an air flow of 3.0 L/minute, and an agitation of 400 rpm.

| *Trace element mixture | |
|---|---|
| $FeSO_4.7H_2O$ | 1 g |
| $MnSO_4.4H_2O$ | 1 g |
| $CoCl_2.2H_2O$ | 0.025 g |
| $CaCl_2$ | 0.1 g |
| $H_3BO_3$ | 0.056 g |
| $(NH_4)_6Mo_7O_2.4H_2O$ | 0.019 g |
| $ZnSO_4.7H_2O$ | 0.2 g |
| distilled water | 1000 ml |

EXAMPLE 1-C

14-Liter Production of 1-681, 512–033 in Stirred Fermentation Vessels.

| Fermentation Medium KF | |
|---|---|
| Tomato paste | 40 g |
| Oat flour | 10 g |
| Corn steep liquor | 5 g |
| Dextrose | 10 g |
| *Trace element mixture | 10 ml |
| Distilled water | |
| Adjusted to pH 6. | |

Seed stage - 1: The entire contents of ATCC 20858 Wt FVM was inoculated into a 250 ml unbaffled erlenmeyer flask containing 50 ml of KF medium sterilized for 20 minutes at 121° C. This flask was cultivated for 53 hours at 28° C. with shaking on a rotary shaker at 220 rpm.

Seed stage - 2: 15 ml of the above inoculum were used to innoculate a second stage seed flask (2 liter unbaffled erlenmeyer flask containing 500 ml of KF medium). The second stage seed was cultivated for 65 hours at 28° C. with shaking on a rotary shaker at 220 rpm.

Production tank: The entire content of seed stage 2 flask was used to inoculate a 14-liter New Brunswick Scientific fermentor containing 9.5 liters of KF medium. The culture was then cultivated for 70 hours at 20° C. at an air flow of 3.0 L/minute, and an agitation of 400 rpm.

| *Trace element mixture | |
|---|---|
| $FeSO_4.7H_2O$ | 1 g |
| $MnSO_4.4H_2O$ | 1 g |
| $CoCl_2.2H_2O$ | 0.025 g |
| $CaCl_2$ | 0.1 g |
| $H_3BO_3$ | 0.056 g |
| $(NH_4)_6Mo_7O_2.4H_2O$ | 0.019 g |
| $ZnSO_4.7H_2O$ | 0.2 g |
| distilled water | 1000 ml |

EXAMPLE 2

Isolation of Elastase Active Compounds from Fermentation Broth L-681,512

The structural formulae of the compounds identified in this example are shown in Table I.

A 14-liter fermentation batch (9 liters) from Example 1-A was filtered through filter aid and the filtrate (pH 7.0, 8.5 liters) was discarded. The solids (0.5 liters) were extracted with 1.5 liters of ethyl acetate three times successively while stirring to yield 4 liters of ethyl acetate extract.

This ethyl acetate extract was taken to dryness under vacuum and dissolved in 10 ml of methylene chloride/methanol (9:1) and charged to a silica gel column (200 g) in methylene chloride/methanol (9:1) and fractionated via the following gradient system:

1. 400 ml methylene chloride/methanol (9:1)
2. 200 ml methylene chloride/methanol (6:1)
3. 200 ml methylene chloride/methanol (4:1)
4. 200 ml methanol The active fraction was in a large broad zone from 1 to 3.2 column volumes. Two large UV spots were observed at Rf 0.4 and Rf 0.2. on silica gel TLC plates using the solvent system 85:15, $CH_2Cl_2$:MeOH.

This active zone was taken to dryness under vacuum and redissolved in 10 mL of the same solvent noted above and rechromatographed on a new 200 g silica gel column using the same gradient system and collection system. Two zones of activity were recovered one at 1–1½ column volumes, zone 1; and one at 1½–2–2¼ column volumes, zone 2. One UV spot was observed by TLC at Rf 0.4 from zone 1 and two UV spots at Rf 0.4 and Rf 0.2 were observed from zone 2 using the same solvent system mentioned above.

Zone 2 from the second silica gel column containing 2 UV spots by TLC, was taken to dryness under vacuum and dissolved in 2 mL of methanol water acetic acid, 90:10:1. A precipitate formed and was filtered off and the solution was charged to a flash reverse phase C 18 column (20 cc) in methanol-water-acetic acid and fractionated. Thirty cuts were taken (4 mL each) and the spot of interest (Rf 0.2) was collected in cuts 9–12 (2–½ column volumes) determined by TLC.

An analytical HPLC system was developed using 23-77, 0.01M tetrabutyl ammonium phosphate (pH 7.2) buffer methanol solvent system at 40° C. on a Zorbax ODS (4.6 mm ×25 cm) column at a flow rate of 2 mL/min. monitored by UV absorption at 250 and 220 nm. Fractions 9-12 from the flash reverse phase column contained a material (Rf 0.2) detected at 250 nm with a retention time of 12.2 minutes, Compound 1, as well as a second compound detected at 220 nm (no absorption at 250 nm) with a retention time of 18.1 minutes, Compound 2.

Cuts 9-12 were evaporated to dryness under vacuum and redissolved in 500 μl methanol and two equivalent runs were made, each with 250 μl of sample on a semi preparative Whatman ODS 3 Magnum 9 column with an 8-2, methanol-1% acetic acid solvent system at 6 mL/min. detecting at 250 and 220 nm. Compound 1 was isolated in cuts 11-14 (6 mL each) and Compound 2 was isolated in cuts 16-18 from each chromatographic run. Analytical HPLC was used to determine purity of compound in each cut. Cuts containing Compound 1 were taken to dryness and had a weight of 12 mg, while the weight of the fractions containing Compound 2 was 8 mg.

Zone 1 from the second silica gel column containing 1 UV spot by TLC, was taken to dryness under vacuum, dissolved in same solvent as zone 2, and charged to an identical flash reverse phase column. Thirty cuts were taken and the UV spot of interest (Rf 0.4) was collected in cuts 6-10 determined by TLC.

The same analytical HPLC system used for zone 2 was also used for zone 1. Fractions 6-10 from the flash reverse phase column contained a material (Rf 0.4) with a retention time of 3.05 minutes absorbing at 250 nm, Compound 3, as well as a material absorbing at 220 nm with a retention time of 9.8 minutes, Compound 4.

Cuts 6-10 were evaporated to dryness and charged to the Magnum 9 Whatman ODS-3 column using the same conditions as for zone 2. Compound 3 was isolated clearly in cut 11 and Compound 4 was isolated in cut 13. Purity was determined by analytical HPLC. The weight of Compound 3, was 10.5 mg, while the weight of Compound 4, was 13.6 mg.

TABLE I

Compounds of Example 2

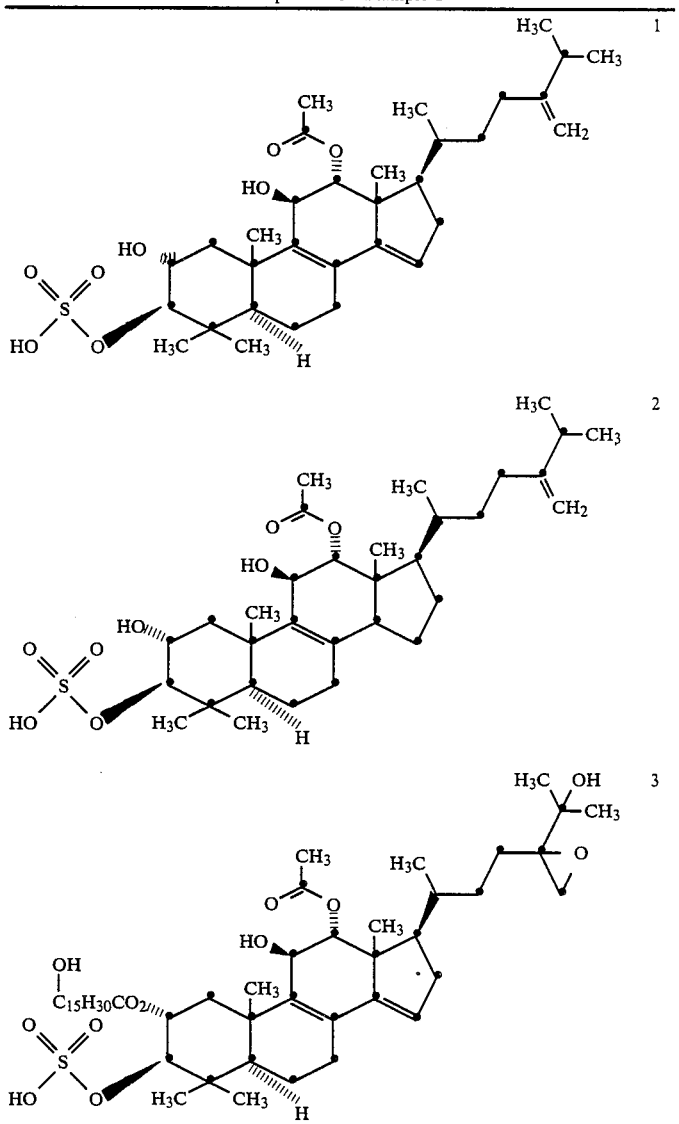

TABLE I-continued
Compounds of Example 2

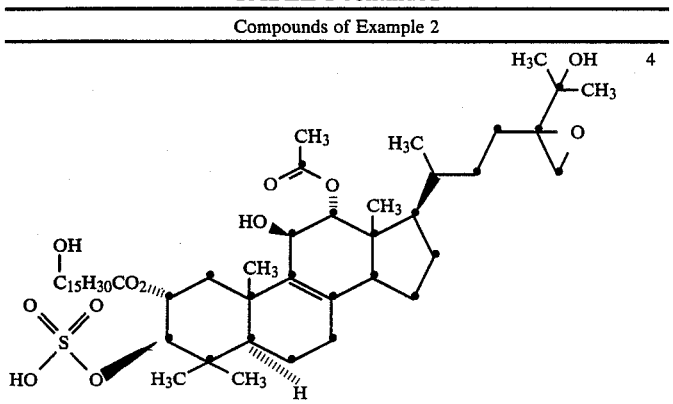

EXAMPLE 3

Isolation of Elastase Active Compounds

The structural formulae of the compounds identified in this example are shown in Table II.

Approximately ⅓ of the methylene chloride extract (67 ml) from the fermentation batch from Example 1-B was charged to a 500 cc silica gel column in 10:90, methanol methylene chloride and fifteen 150 ml cuts were taken employing the following solvents: 1 liter of 10:90, 1 liter of 20:80 and 1 liter of methanol. Compound 5 was isolated in cuts 1–5 as determined by HPLC using a Whatman ODS 3 analytical column detecting at 250 and 220 nm at 40° C. using a 30:70, water acetonitrile solvent system. The remaining ⅔ of the methylene chloride extract was taken to dryness, dissolved in methanol and was charged to a 600 cc Sephadex LH-20 column in methanol and Compound 5 was isolated in cuts 3–10. Partitioning between hexane and water further purified Compound 5. The hexane extract containing Compound 5 was added to the Compound 5 isolated from the above silica column and this was charged to a 600 cc silica column in 95:5, methylene chloride:methanol and Compound 5 was isolated in cuts 35–90, while a new related material, Compound 6, was isolated in cuts 22–35.

Crude Compound 5 in 80 ml of methanol was charged to a 4 liter Sephadex LH-20 column and 20 ml cuts taken, analyzed by TLC and the compound was found in cuts 130 –190 along with Compound 6. This material (15 mL) was charged to a 1 liter silica gel column in 50:50, hexane:ethyl acetate monitored by UV and RI and 20 mL cuts taken and Compound 5 isolated in cuts 220–300, while Compound 6 was isolated in cuts 81–115.

The zone containing Compound 5 was charged to a Zorbax ODS HPLC preparative column in 10:90, water:methanol, 10 mL cuts collected and Compound 5 isolated in cuts 25–29 from combined chromatographies. Compound 7 was isolated in cuts 30–38.

Compound 5 was rechromatographed on the Zorbax ODS preparative column using the same conditions as described above and then on a small Sephadex LH-20 column in 50:50, methylene chloride: <methanol to yield 60 mg of Compound 5.

Cuts 81–115 containing Compound 6 was taken to dryness under vacuum and dissolved in methanol and charged to a Zorbax ODS preparative HPLC column and isolated in cuts 24–28 in duplicate runs (27 mg).

Compound 8 was isolated in cuts 35–40 of this same isolation.

Upon purification of Compound 7, another related material, Compound 9, was isolated in a very small amount.

| Chromatographic Data of Compounds | | | |
|---|---|---|---|
| | | Rf. | |
| Compound | *R.T. (min.) | +silica | =R.P. |
| 5** | 8.65 | .50 | .25 |
| 6 | 12.4 | .48 | .39 |
| 7 | 12.75 | .40 | .37 |
| 8 | 19.7 | .51–.55 | .32–.29 |
| 9 | 10.8 | | |

*retention time on a Whatman ODS 3, 30:70, $H_2O$—$CH_3CN$, 2 ml/min. 40° C.
+silica-gel TLC, 95:5, methylene chloride:methanol
=reverse phase TLC, 95:5, methanol water
**silica gel TLC, 90:10, methylene chloride:methanol
**reverse phase TLC, 90:10, methanol:water

TABLE II
Compounds of Example 3

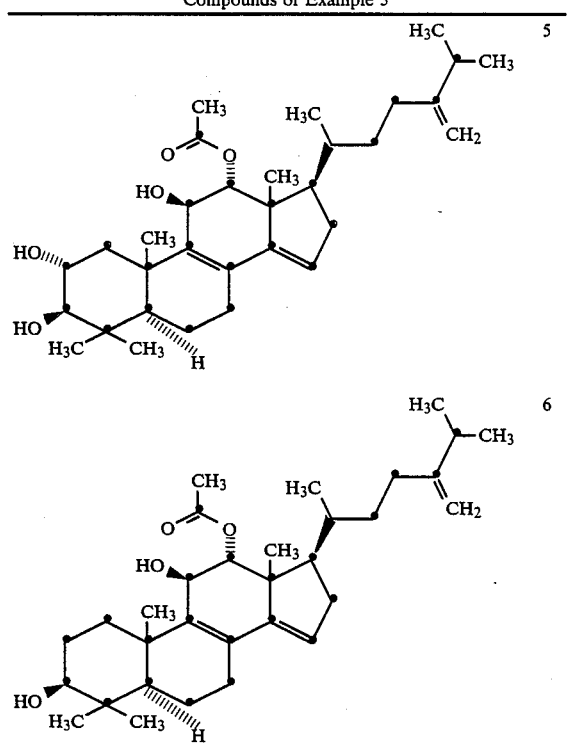

TABLE II-continued
Compounds of Example 3

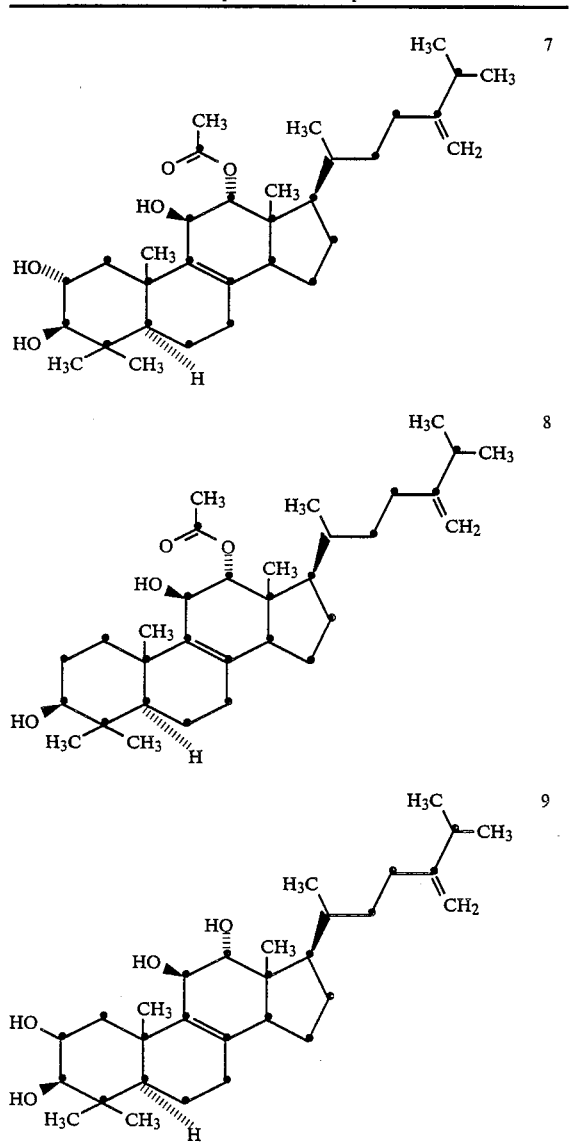

EXAMPLE 4

Preparation of Acetate Ester of Compound 1 (TABLE I)

The structural formula of the compound identified in this example is shown in Table III.

Twenty (20) mg of Compound 1 was dissolved in 12 mL of pyridine and then 28 mL of acetic anhydride was added, stirred and capped. After 24 hours, the reaction at room temperature was 90% completed as judged by TLC analysis. The reaction was stopped after 30 hours, taken to dryness under vacuum, dissolved in methanol and purified on a Whatman ODS-3 Magnum 9 column using a 35:65 water:methanol solvent system. Compound 10 was obtained, analyzed, dried and weighed.

EXAMPLE 5

Other Reactions and Products

The structural formulae of the compounds identified in this example are also shown in Table III.

Using the methods listed below, additional compounds of the invention were obtained.

| Method | Compound Obtained |
| --- | --- |
| Hydrolysis of Compound 1 | 11 |
| Solvolysis of Compound 1 | 5 (Example 3, TABLE II) |
| Solvolysis of Compound 11 | 12 |
| Hydrolysis of Compound 5 | 12 |
| MnO$_2$ oxidation of Compound 2 | 13 |
| Succinate of Compound 5 | 14 |

TABLE III
Compounds of Examples 4 and 5

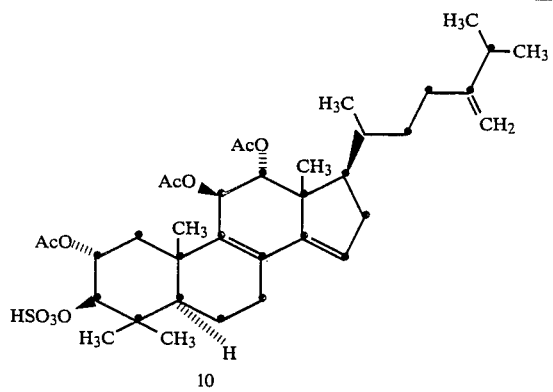

TABLE III-continued
Compounds of Examples 4 and 5
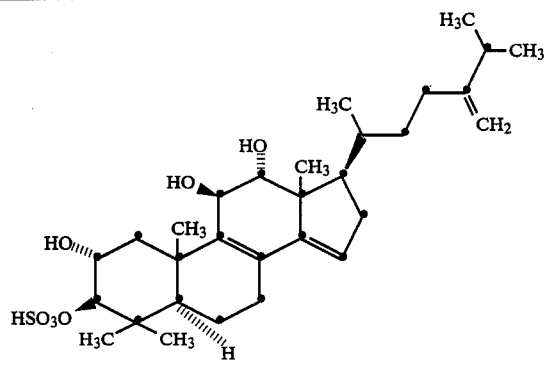
11
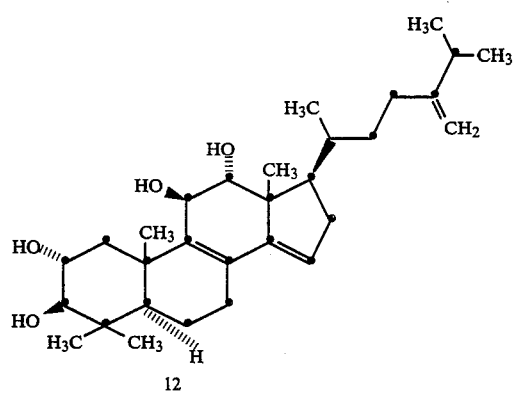
12
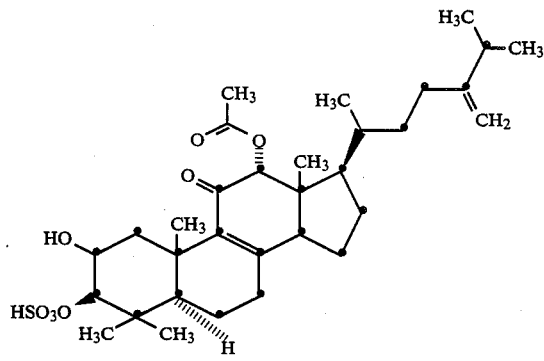
13
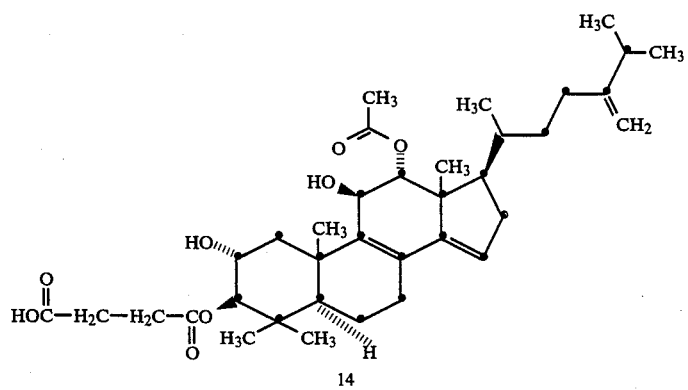
14

EXAMPLE 6

Isolation of Additional Elastase Active Compounds

Two 14 liter isolation batches 18 liters) from Example (1-C) were worked up in a similar manner to Example 2.

The fermentation broth was filtered and the cake extracted with ethyl acetate. The extract was dried, dissolved in 50 mL of methylene chloride and charged to a silica gel column (400 g) employing a 8.5:12.5, methylene chloride:methanol solvent system in which the compounds eluted at ⅓ to 1 column volume in cuts 7–16 detected by UV and RI. The active zone was taken to dryness, dissolved in 10 mL methylene chloride, charged to a second silica gel column (200 g) in 95:5, methylene chloride:methanol and eluted with 95:5 for nine 100 mL cuts and then 90:10 for eight 100 mL cuts. The actual zone, cuts 11–12, was determined to contain two compounds by TLC and HPLC. This active zone was dissolved in 3 mL of methanol, solids discarded and solution charged to a 21 mm×25 cm Zorbax reverse phase HPLC column at 40° C. and eluted with a 35:65 water:methanol solvent system. Cuts 48–51 contained Compound 15, (RT 8.1) min.) while cuts 52 end contained Compound 16 (RT 10.1 min ).

The structural formulae for these compounds are shown in Table IV.

Mass Spectral Data

Low resolution mass spectra were recorded on a Finnigan-MAT212 mass spectrometer in the electron impact mode (EI, 90 eV). Exact mass measurements were made on the same instrument at high resolution by the peak matching method using perfluorokerosene (PFK) as internal standard. Negative ion Fast Atom Bombardment [(−)FAB] spectra were obtained on a MAT-731 mass spectrometer.

Six of the compounds contain sulfate moieties. The molecular ion was not observed in the EI mass spectra of the sulfated compounds. The highest mass ion observed corresponds to $M-H_2SO_4$ and major fragment ions result from $M-H_2SO_4-CH_3CO_2H$ and $M-H_2SO_4-CH_3CO_2H-H_2O$. By negative ion FAB, the sulfated compounds all afforded pseudo molecular ions corresponding to $(M-H)^-$ allowing assignment of molecular weight and empirical formula.

The remaining non-sulfated compounds all exhibited a molecular ion in their EI mass spectra. Major fragment ions correspond to $M-CH_3CO_2H$ and $M-CH_3CO_2H-H_2O$ as was similarly observed for the sulfated compounds.

TABLE IV
Compounds of Example 6

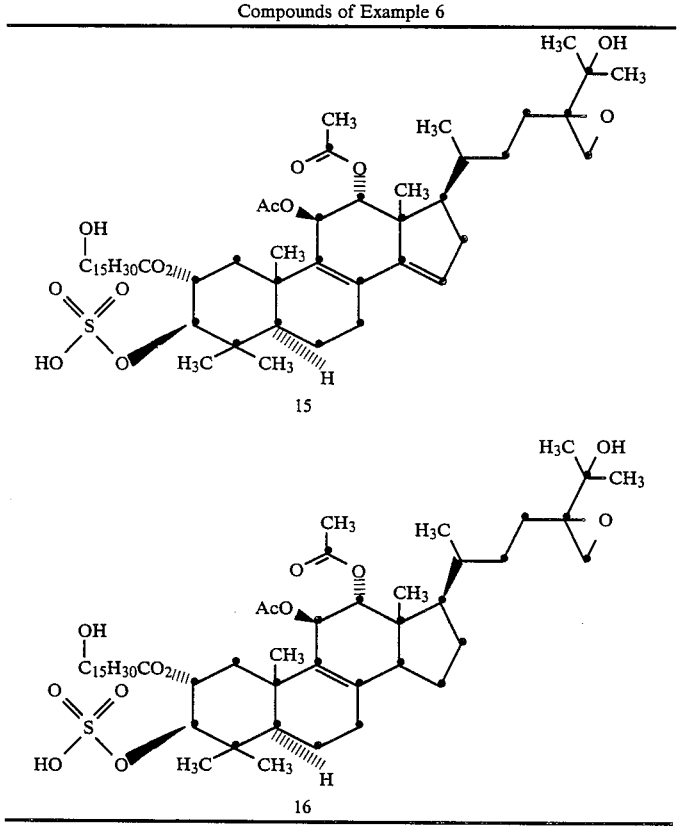

EXAMPLE 7

Characterization and Structures of Derivatives Obtained from the Culture Producing L-681,512

The following mass spectral (MS) and nuclear magnetic resonance (NMR) data characterize the natural products isolated from 681,512. The structures of the compounds were assigned based upon interpretation of their spectral data.

The data obtained is listed below:

| Compound | M.W. | Emp. Formula | M.W. Confirmation |
|---|---|---|---|
| 1 | 594 | $C_{32}H_{50}O_8S$ | (−)FAB m/z 593 |
| 2 | 596 | $C_{32}H_{52}O_8S$ | (−)FAB m/z 595 |
|   | 922 | $C_{50}H_{82}O_{13}S$ | (−)FAB m/z 921 |

-continued

| Compound | M.W. | Emp. Formula | M.W. Confirmation |
|---|---|---|---|
|  | 924 | $C_{50}H_{84}O_{13}S$ | (−)FAB m/z 923 |
| 3 | 880 | $C_{48}H_{80}O_{12}S$ | (−)FAB m/z 879 |
| 4 | 882 | $C_{48}H_{82}O_{12}S$ | (−)FAB m/z 881 |
| 5 | 514 | $C_{32}H_{50}O_5$ | EI $M^+$ m/z 514 |
| 6 | 498 | $C_{32}H_{50}O_4$ | EI $M^+$ m/z 498 |
| 7 | 516 | $C_{32}H_{52}O_5$ | EI $M^+$ m/z 516 |
| 8 | 500 | $C_{32}H_{52}O_4$ | EI $M^+$ m/z 500 |
| 9 | 470 | $C_{30}H_{46}O_4$ | EI $M^+$ m/z 470 |
| 11 | 552 | $C_{30}H_{48}O_7S$ | (+)FAB m/z 597 ($M^+$ + $Na_2$) |
| 12 | 472 | $C_{30}H_{48}O_4$ | EI $M^+$ m/z 472 |
| 15 | 922 | $C_{50}H_{82}O_{13}S$ | (−)FAB m/z 921 |
| 16 | 924 | $C_{50}H_{84}O_{13}S$ | (−)FAB m/z 923 |

The following high resolution-mass spectroscopy (HR-MS) measurements were obtained:

| Compound | Found | Calcd. | Formula | Assignment |
|---|---|---|---|---|
| 1 | 496.3553 | 496.3553 | $C_{32}H_{48}O_4$ | $(M-s)^+$ |
|  | 436.3350 | 436.3341 | $C_{30}H_{44}O_2$ |  |
|  | 293.1910 | 293.1905 | $C_{21}H_{25}O$ |  |
| 2 | 438.3506 | 438.3498 | $C_{30}H_{46}O_2$ | $(M-s-a)^+$ |
|  | 295.2067 | 295.2062 | $C_{21}H_{27}O$ |  |
| 3 | 704.5389 | 704.5380 | $C_{46}H_{72}O_5$ | $(M-s-a-h)^+$ |
|  | 547.4127 | 547.4151 | $C_{37}H_{55}O_3$ |  |
|  | 450.3142 | 450.3134 | $C_{30}H_{42}O_3$ |  |
| 4 | 706.5535 | 706.5536 | $C_{46}H_{74}O_5$ | $(M-s-a-h)^+$ |
|  | 549.4306 | 549.4308 | $C_{37}H_{57}O_3$ |  |
|  | 452.3293 | 452.3290 | $C_{30}H_{44}O_3$ |  |
|  | 295.2041 | 295.2062 | $C_{21}H_{27}O$ |  |
| 5 | 454.3439 | 454.3447 | $C_{30}H_{46}O_3$ | $(M-a)^+$ |
| 6 | 438.3493 | 438.3498 | $C_{30}H_{46}O_2$ |  |
|  | 423.3262 | 423.3263 | $C_{29}H_{43}O_2$ | $(M-a)^+$ |
| 7 | 516.3814 | 516.3815 | $C_{32}H_{52}O_5$ | $M^+$ |
| 8 | 500.3868 | 500.3866 | $C_{32}H_{52}O_4$ | $M^+$ |
| 9 | 470.3397 | 470.3396 | $C_{30}H_{46}O_4$ | $M^+$ |

Note:
s = $H_2SO_4$;
a = $CH_3CO_2H$;
and h = $H_2O$

$^1$H-NMR Spectral Data

The spectra were recorded at ambient room temperature on a Varian SC-300 NMR spectrometer. These data are shown in FIGS. 1–5 for compounds 1–4 and 6, respectively.

BIOLOGICAL EVIDENCE IN SUPPORT OF UTILITY OF THE INVENTION

Background

One of the most common enzyme assay methods presently followed is typically referred to as a "one point" assay. This method requires separately preparing a control blank; preparing the enzyme samples to be screened; determining the color reading obtained from the enzyme samples; and individually comparing the enzyme sample colors against that of the control blank to not only determine activity, but also determine the degree of activity.

Commercial apparatus, such as the Titertek ® Multiskan, are available to accept 96 enzyme samples to be screened. While such apparatus enables one to obtain a color reading of these enzyme samples within about one minute, excessive time must then be spent individually comparing each enzyme sample with the previously, separately prepared control blank in screening the enzyme samples for activity.

Thus, while such commercial apparatus afford a fast initial color reading of the enzyme samples, the ensuing comparison of them with the control blank is time consuming and does not result in an accurate screening.

Two Point or "Zero Time" Assay

It has now been found that the short comings of the assay methods described above are overcome by employing a newly developed two point or "zero time" assay method. This new, two point assay method is readily adaptable for use with commercial enzyme screening-apparatus such as the Titertek ® Multiskan mentioned above so that no new or additional apparatus are needed to employ the two point assay method.

In general, the new, two point assay method for screening enzyme activity comprises: preparing a plurality of control blanks; preparing a plurality of screening blanks by charging thereto samples of the desired enzymes; charging to the blanks containing the desired enzymes samples of enzyme inhibitors from each fermentation broth to be screened; noting the time and adding a chromogenic medium to all blanks; permitting a predetermined period of time to elapse; and, measuring the color of each blank to immediately determine which fermantation samples exhibit the desired enzyme inhibition activity and the degree of said activity.

When the foregoing, two point assay method is used with commercial apparatus, the term "wells" can be substituted for the term "blanks" as these apparatus contain wells to accept the control substances, the desired enzyme samples, and the samples of enzyme inhibitor from the fermentation broth.

Although several control blanks or wells can be prepared, such as from about 2–5, typically only about 2–3 control wells are used.

It is generally understood that the enzyme of interest is that enzyme against which the inhibitory activity of the fermentation broth samples are being determined and quantified (e.g., PMN elastase). Consequently, all of the remaining wells are charged with the same enzyme of interest. However, several enzymes of interest can be charged to a plurality of wells, and the wells grouped together to facilitate separate identification and assay. When this is done, separate control wells must then also be prepared to correspond to the different enzymes of interest.

The fermentation broth samples charged to the enzyme containing wells are typically taken from the extract of each broth; e.g., the methanol broth extract.

The chromogenic medium is charged to all the wells at substantially the same time and the time of this addition is noted. This is the "zero time" mentioned earlier as it is from that moment that a predetermined time lapse is measured during which sufficient reaction between the fermentation broth samples and the enzyme of interest occurs to enable not only accurate screening of enzyme inhibitory activity, but also the degree of that activity. Naturally, the predetermined time lapse will differ with different enzymes and can be from about 1 minute to about 20 minutes, typically from about 2 minutes to about 10 minutes.

The chromogenic media typically used are aromatic nitro- containing compounds. Illustrative of such compounds are Boc-ala-ala-pro-ala-p-nitroanilide, -α-benzoyl-DL-arginine-p-nitroanilide, N-α-benzoyl-L-tyrosine-p-nitroanilide, and the like.

Using the two point or "zero time" assay method described above, the following protocol was employed:

PROTOCOL

Enzyme Assays for the Inhibition of Human Polymorphonuclear Leukocyte Elastase Via Hydrolysis of N-t-Boc-alanyl-alanyl-prolylalanine-p-nitroanilide Reagents 0.05M TES (N-tris[hydroxymethyl]methyl-2amino ethanesulfonic acid) Buffer, pH 7.5.

0.2 mM N-t-Boc-alanyl-alanyl-prolyl-alaninep-nitroanilide (Boc AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (cephalosporin sulfone esters) to be tested dissolved in DMSO just before use.

Assay Procedure

To 1.0 ml of 0.2 mM Boc-AAPAN in a cuvette, 0.01–0.1 ml of DMSO with or without inhibitor was added. After mixing, a measurement was taken at 410 nm to detect any spontaneous hydrolysis due to presence of test compound. 0.05 Milliliters of PMN extract was then added and the ΔOD/min at 410 nm was measured and recorded. A Beckman model 35 spectrophotometer was used.

Results

Results were reported as $ED_{50}$, i.e., effective dosage in micrograms per milliliter (μg/ml) for 50% inhibition of the enzyme activity 2 minutes after zero time.

Comments

The elastase activity in the crude PMN extract may vary from one preparation to another. A control of each new batch is run, and the volume added in the assay procedure is adjusted according to activity.

The biological results for representative compounds of the invention are shown in Table V below.

TABLE V

Biological Results for Representative Compounds of the Invention

| Compound of the Invention | $ED_{50}$ (μg/ml) |
| --- | --- |
| 1 | 1.4 |
| 2 | 1.5 |
| 3 | 1.7 |
| 4 | 1.4 |
| 5 | 0.9 |
| 10 | 178 |
| 11 | 1.9 |

What is claimed is:

1. A method of treating inflammation and degeneration in mammals which comprises administering to a mammal in need of such treatment an anti-inflammatory and antidegenerative amount a compound having the formula:

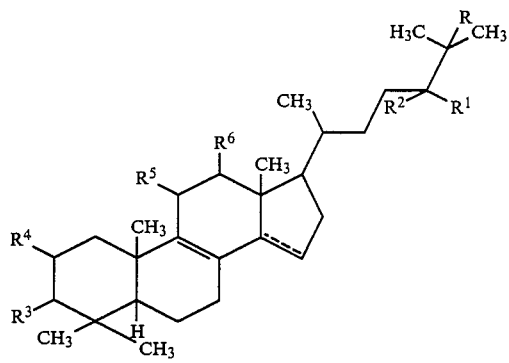

wherein:
R is OH or is absent;
$R^1$ and $R^2$ together form $=CH_2$, $-CH_2O-$;
$R^3$ is OH, $HSO_3O$, $HOCOCH_2CH_2CO_2$;
$R^4$ is OH, $HOC_{15}H_{30}CO_2$, AcO, or is absent
$R^5$ is $=O$, OH, AcO; and
$R^6$ is $CH_3$, OH, AcO.

2. The method of claim 1 wherein said compound is a member selected from the group:

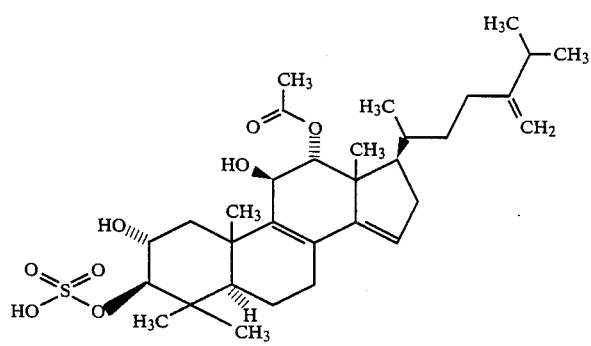

1

-continued
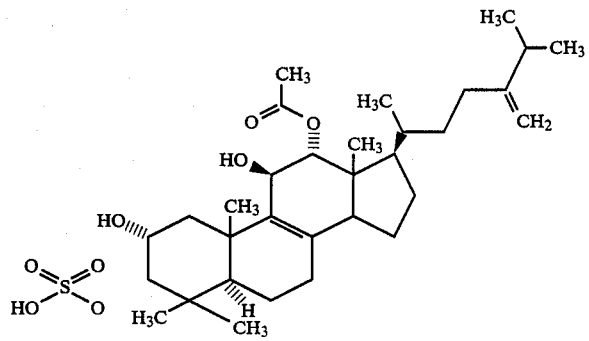
2
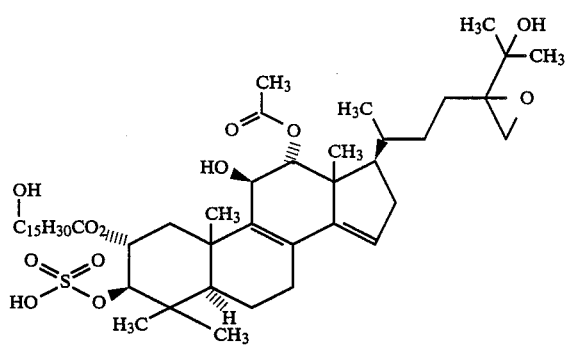
3
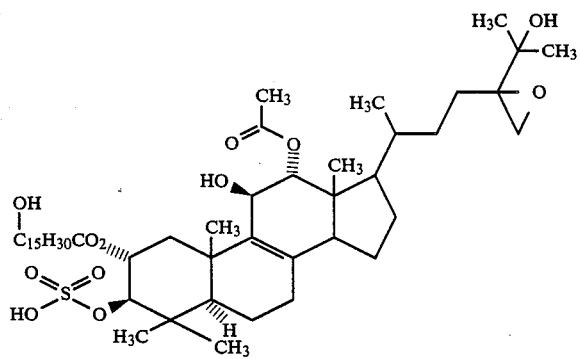
4
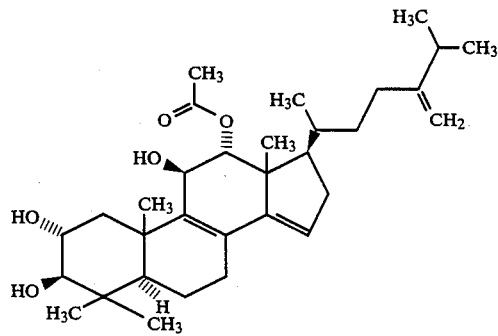
5

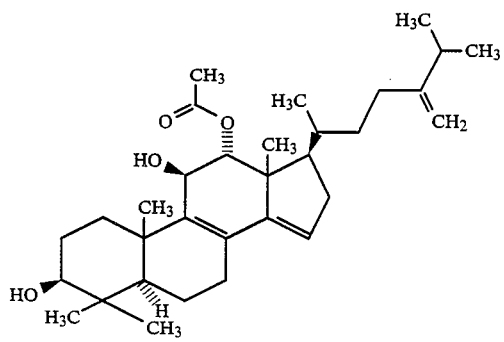
6
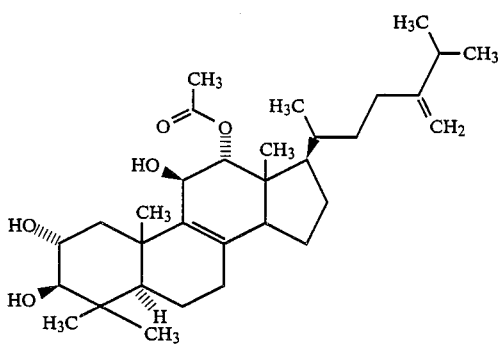
7
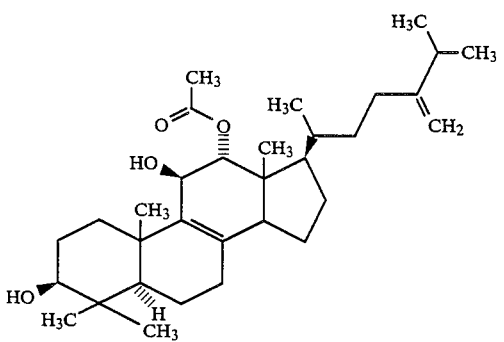
8
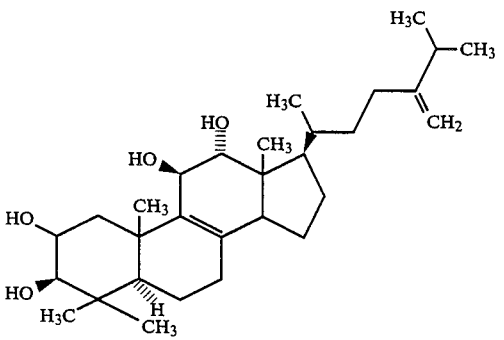
9

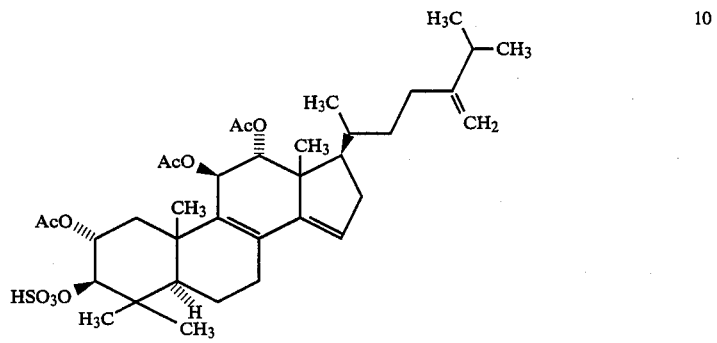
10
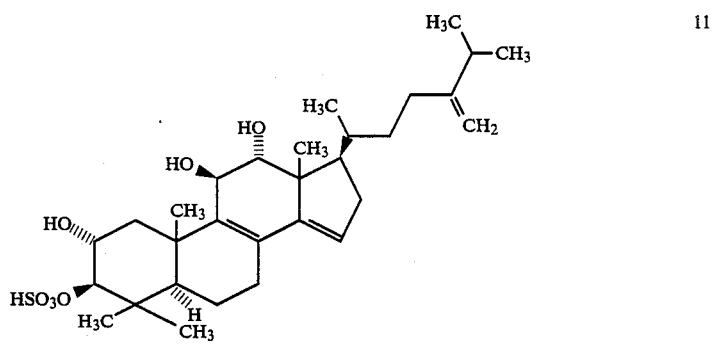
11
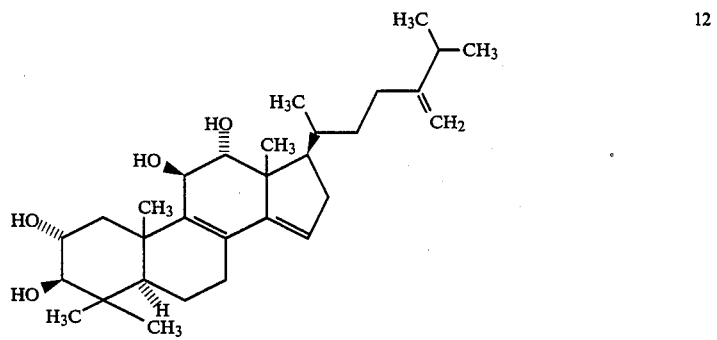
12
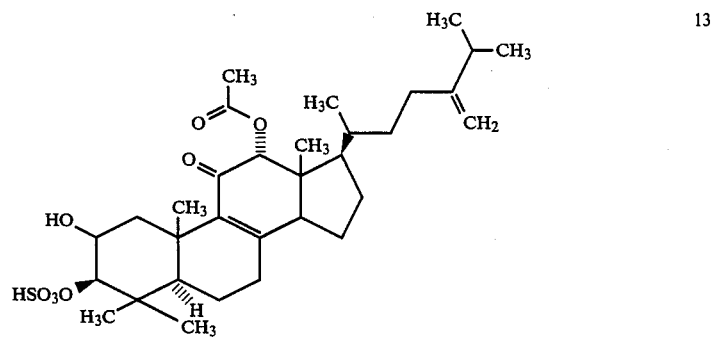
13

-continued
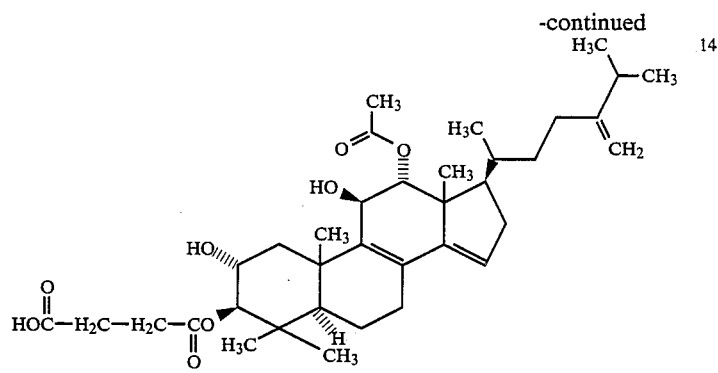
14
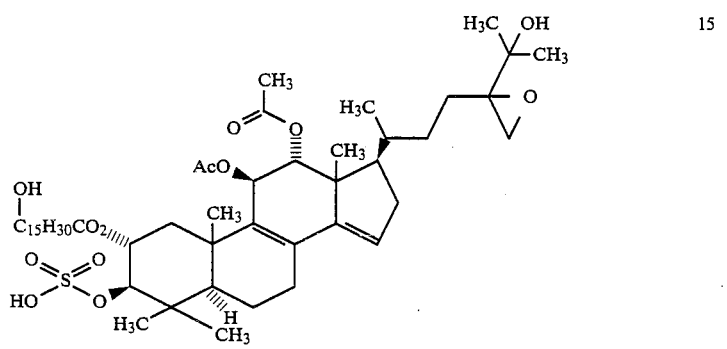
15
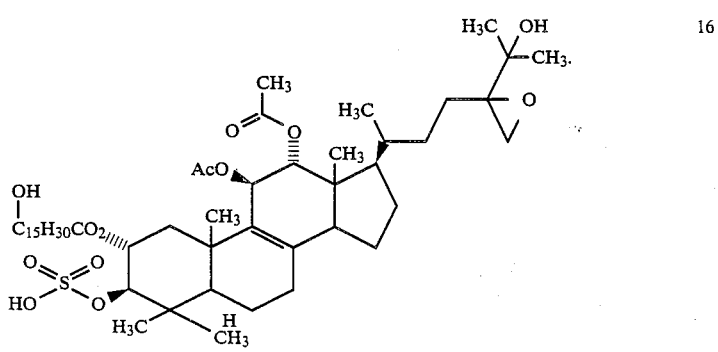
16